(12) United States Patent
Gu et al.

(10) Patent No.: US 11,072,574 B2
(45) Date of Patent: Jul. 27, 2021

(54) METHOD FOR DEGRADING PERFLUORINATED COMPOUNDS

(71) Applicant: Nanjing University, Nanjing (CN)

(72) Inventors: Cheng Gu, Nanjing (CN); Zhanghao Chen, Nanjing (CN); Chen Li, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 16/925,038

(22) Filed: Jul. 9, 2020

(65) Prior Publication Data

US 2021/0047256 A1    Feb. 18, 2021

(30) Foreign Application Priority Data

Jan. 14, 2020    (CN) .......................... 202010037007.6

(51) Int. Cl.
  *C07C 51/377*    (2006.01)
(52) U.S. Cl.
  CPC .................................. *C07C 51/377* (2013.01)
(58) Field of Classification Search
  CPC ................................................. C07C 51/377
  See application file for complete search history.

(56) References Cited

PUBLICATIONS

Chen et al. Feb. 2020 (Efficient Reductive Destruction of Perfluoroalkyl Substances under Self-Assembled Micelle Confinement, Environmental Science and Technology, 54, pp. 5178-5185, Published Feb. 2020. (Year: 2020).*
Supporting information Chen et al. Feb. 2020 (Efficient Reductive Destruction of Perfluoroalkyl Substances under Self-Assembled Micelle Confinement, Environmental Science and Technology, 54, pp. 5178-5185, Published Feb. 2020). (Year: 2020).*
Chen et al. (Effects of Different Variables on Photodestruction of Perfluorooctanoic acid in sefl-assembled micelle system, Science of the Total Environment 742, pp. 1-9, Published Jun. 2020) (Year: 2020).*
Jing et al. (Photodegradation of perfluorooctanoic acid by 185 nm vacuum ultraviolet light, J. of Environmental Sciences, 19, pp. 387-390, Published 2007) (Year: 2007).*
Paul, A. G. et al.," A First Global Production, Emission, and Environmental Inventory for Perfluorooctane Sulfonate." Environmental science & technology, 2009, 43, (2), 386-392. Published on Web Dec. 11, 2008.

Wang, Z. et al.., "Global emission inventories for C-4-C-14 perfiuoroalkyl carboxylic acid (PFCA) homologues from 1951 to 2030, part II: The remaining pieces of the puzzle." Environment international 69, 2014, 166-176.
Renner, R., "Evidence of toxic effects and environmental impacts has sent researchers scrambling to obtain more data." Environmental science & technology, Apr. 1, 2001, 35, (7), 154A-160A.
Giesy, J. P. et al., "Perfluorochemical surfactants in the environment." Environmental science & technology, Apr. 1, 2002, 36, (7), 146A-152A.
Hansen, K. J. et al., "Quantitative characterization of trace levels of PFOS and PFOA in the Tennessee River." Environmental science & technology 36, 2002, (8), 1681-1685.
Koustas, E. et al., "The Navigation Guide—evidence-based medicine meets environmental health: systematic review of nonhuman evidence for PFOA effects on fetal growth." Environmental health perspectives,Oct. 1, 2014, 122, (10), 1015-27.
Stein, C. R. et al., "Serum Perfluorinated Compound Concentration and Attention Deficit/Hyperactivity Disorder in Children 5-18 Years of Age." Environmental health perspectives, Oct. 2011, 119, (10), 1466-1471.
Wang, T. et al., "Perspectives on the Inclusion of Perfluorooctane Sulfonate into the Stockholm Convention on Persistent Organic Pollutants." Environmental science & technology, 2009, 43, (14), 5171-5175. Published on Web Jun. 8, 2009.
Hu, X. C. et al., "Detection of Poly- and Perfluoroalkyl Substances (PFASs) in US Drinking Water Linked to Industrial Sites, Military Fire Training Areas, and Wastewater Treatment Plants." Environmental Science & Technology Letters, 2016, 3, (10), 344-350.
Park, H. et al., "Reductive Defluorination of Aqueous Perfluorinated Alkyl Surfactants: Effects of Ionic Headgroup and Chain Length." Journal of Physical Chemistry A, 2009, 113, (4), 690-696. Published on Web Jan. 5, 2009.
O'Hagan, D., "Understanding organofluorine chemistry. An introduction to the C—F bond." Chemical Society Reviews 37, 2008, (2), 308-319. Published on the web Oct. 17, 2007.

(Continued)

*Primary Examiner* — Yevgeny Valenrod
*Assistant Examiner* — Blaine G Doletski (57) ABSTRACT

The present invention discloses a method for degrading perfluorinated compounds (PFCs) and belongs to the field of degradation of persistent pollutants. According to the present invention, cetyltrimethylammonium bromide (CTAB), indoleacetic acid (IAA) and PFCs are mixed to form compact self-assembled micelles, and the self-assembled micelles are illuminated, so that PFCs are rapidly degraded and defluorinated in the micelles, thereby realizing the degradation of PFCs by using a novel self-assembled micelle system and improving the degradation efficiency of PFCs.

7 Claims, 12 Drawing Sheets

(56) References Cited

PUBLICATIONS

Schroder, H. Fr. et al., "Stability of fluorinated surfactants in advanced oxidation processes—A follow up of degradation products using flow injection-mass spectrometry, liquid chromatography-mass spectrometry and liquid chromatography-multiple stage mass spectrometry." Journal of Chromatography A, 1082, Mar. 7, 2005, pp. 110-119.

Luo, Qi et al., "Perfluorooctanesulfonate Degrades in a Laccase-Mediator System." Environmental science & technology, 2018, 52, (18), 10617-10626.

Tang, H. et al., "Efficient degradation of perfluorooctanoic acid by UV-Fenton process." Chemical Engineering Journal 184, 2012, pp. 156-162.

Tian, H. et al., "Complete Defluorination of Perfluorinated Compounds by Hydrated Electrons Generated from 3-Indole-acetic-acid in Organomodified Montmorillonite." Scientific reports 6:32949, 1-9. Published on Sep. 9, 2016.

Song, Z. et al., "Reductive defluorination of perfluorooctanoic acid by hydrated electrons in a sulfite-mediated UV photochemical system." Journal of hazardous materials 262, 2013, pp. 332-338.

\* cited by examiner

METHOD FOR DEGRADING PERFLUORINATED COMPOUNDS

TECHNICAL FIELD

The present invention belongs to the field of degradation of persistent pollutants, and more particularly, relates to a method for degrading perfluorinated compounds (PFCs).

BACKGROUND

PFCs are a series of synthetic chemicals. Since perfluorooctanoic acid (PFOA) was successfully synthesized for the first time by 3M in the 1950s, it has received extensive attention in many fields. However, its massive production and use make the problem of PFCs pollution in surface water and groundwater more and more serious (Paul, A. G.; Jones, K. C.; Sweetman, A. J., A First Global Production, Emission, And Environmental Inventory For Perfluorooctane Sulfonate. Environmental science & technology 2009, 43, (2), 386-392. Wang, Z.; Cousins, I. T.; Scheringer, M.; Buck, R. C.; Hungerbuehler, K., Global emission inventories for C-4-C-14 perfluoroalkyl carboxylic acid (PFCA) homologues from 1951 to 2030, part II: The remaining pieces of the puzzle Environment international 2014, 69, 166-176. Renner, R., Evidence of toxic effects and environmental impacts has sent researchers scrambling to obtain more data. Environmental science & technology 2001, 35, (7), 154A-160A. Giesy, J. P.; Kalman, K., Perfluorochemical surfactants in the environment. Environmental science & technology 2002, 36, (7), 146A-152A).

Recently, some scholars have found that PFCs not only have negative effects on the ecological environment, but also can cause human health problems such as liver and kidney damage, cancer, and affect normal embryo growth and development, etc. (Hansen, K. J.; Johnson, H. O.; Eldridge, J. S.; Butenhoff, J. L.; Dick, L. A., Quantitative characterization of trace levels of PFOS and PFOA in the Tennessee River. Environmental science & technology 2002, 36, (8), 1681-1685. Nakayama, S.; Harada, K.; Inoue, K.; Sasaki, K.; Seery, B.; Saito, N.; Koizumi, A., Distributions of perfluorooctanoic acid (PFOA) and perfluorooctane sulfonate (PFOS) in Japan and their toxicities. Environmental sciences: an international journal of environmental physiology and toxicology 2005, 12, (6), 293-313. Koustas, E.; Lam, J.; Sutton, P.; Johnson, P. I.; Atchley, D. S.; Sen, S.; Robinson, K. A.; Axelrad, D. A.; Woodruff, T. J., The Navigation Guide—evidence-based medicine meets environmental health: systematic review of nonhuman evidence for PFOA effects on fetal growth. Environmental health perspectives 2014, 122, (10), 1015-27). In order to better control this pollutant, the international community has already listed PFCs on the pollutant priority control list of Stockholm Convention. At the same time, U.S. Environmental Protection Agency has also set health risk values ($<70$ ng $L^{-1}$) for PFOA and perfluorooctanesulfonic acid (PFOS) in drinking water. Although all parties are trying to control the environmental problems caused by PFCs, some environmental problems caused by PFCs are still emerging. For example, Michigan declared a state of emergency in 2018 because of PFCs pollution in tap water.

Perfluorinated molecules usually consist of two parts, a fluorinated alkyl chain tail and an ionic functional group head (Stein, C. R.; Savitz, D. A., Serum Perfluorinated Compound Concentration and Attention Deficit/Hyperactivity Disorder in Children 5-18 Years of Age. Environmental health perspectives 2011, 119, (10), 1466-1471. Wang, T.; Wang, Y.; Liao, C.; Cai, Y.; Jiang, G., Perspectives on the Inclusion of Perfluorooctane Sulfonate into the Stockholm Convention on Persistent Organic Pollutants. Environmental science & technology 2009, 43, (14), 5171-5175). Such structures make PFCs generally have hydrophobic and lipophobic properties. In addition, due to the high bond energy (485 kJ/mol) of fluorocarbon bonds (Hu, X. C.; Andrews, D. Q.; Lindstrom, A. B.; Bruton, T. A.; Schaider, L. A.; Grandjean, P.; Lohmann, R.; Carignan, C. C.; Blum, A.; Balan, S. A.; Higgins, C. P.; Sunderland, E. M., Detection of Poly- and Perfluoroalkyl Substances (PFASs) in US Drinking Water Linked to Industrial Sites, Military Fire Training Areas, and Wastewater Treatment Plants. Environmental Science & Technology Letters 2016, 3, (10), 344-350), PFCs show strong structural stability (Park, H.; Vecitis, C. D.; Cheng, J.; Choi, W.; Mader, B. T.; Hoffmann, M. R., Reductive Defluorination of Aqueous Perfluorinated Alkyl Surfactants: Effects of Ionic Headgroup and Chain Length. Journal of Physical Chemistry A 2009, 113, (4), 690-696).

Although the strong stability expands the application of PFCs, it also makes PFCs have strong resistance to chemical and biological degradation. With regard to common advanced oxidation technologies, photocatalytic technologies and electrochemical technologies, some practical problems, including reaction efficiency and technical costs, limit their promotion (O'Hagan, D., Understanding organofluorine chemistry. An introduction to the C—F bond. Chemical Society Reviews 2008, 37, (2), 308-319. Schroder, H. F.; Meesters, R. J. W., Stability of fluorinated surfactants in advanced oxidation processes—A follow up of degradation products using flow injection-mass spectrometry, liquid chromatography-mass spectrometry and liquid chromatography-multiple stage mass spectrometry. Journal of Chromatography A 2005, 1082, (1), 110-119). The adsorption technologies based on activated carbon or ion exchange resin still need to be improved in efficiency and selectivity (Luo, Q.; Yan, X.; Lu, J.; Huang, Q., Perfluorooctanesulfonate Degrades in a Laccase-Mediator System. Environmental science & technology 2018, 52, (18), 10617-10626. Tang, H.; Xiang, Q.; Lei, M.; Yan, J.; Zhu, L.; Zou, J., Efficient degradation of perfluorooctanoic acid by UV-Fenton process. Chemical Engineering Journal 2012, 184, 156-162.).

At present, advanced reduction technologies based on reductive active species such as hydrated electrons have been proved to effectively degrade PFCs, but their low adaptability to the environment and low reaction rate with PFCs also limit their promotion and use (Tian, H.; Gao, J.; Li, H.; Boyd, S. A.; Gu, C., Complete Defluorination of Perfluorinated Compounds by Hydrated Electrons Generated from 3-Indole-acetic-acid in Organomodified Montmorillonite. Scientific reports 2016, 6, 32949. Song, Z.; Tang, H.; Wang, N.; Zhu, L., Reductive defluorination of perfluorooctanoic acid by hydrated electrons in a sulfite-mediated UV photochemical system. Journal of hazardous materials 2013, 262, 332-8).

SUMMARY

1. Problems to be Solved

In view of the problem of low degradation efficiency in existing PFC degradation technologies, the present invention provides a method for degrading PFCs. According to the present invention, positively charged cationic surfactant cetyltrimethylammonium bromide (CTAB) is added into negatively charged indoleacetic acid (IAA) and PFCs solution, the mutually exclusive IAA and PFCs are connected with each other by utilizing the bridging effect of the CTAB to form compact self-assembled micelles, and then the self-assembled micelles are illuminated by a high-voltage mercury lamp, so that PFCs can be rapidly degraded in the micelles, thereby improving the degradation efficiency of PFCs.

2. Technical Solution

In order to solve the foregoing problems, the technical solutions adopted by the present invention are as follows:

A method for degrading PFCs according to the present invention, comprising the following steps:

S10: uniformly mixing CTAB, IAA and PFCs to obtain ternary mixed self-assembled micelles; and S20: illuminating the ternary mixed self-assembled micelles obtained in step S10 by a high-voltage mercury lamp to implement photoreaction to degrade PFCs.

Preferably, in step S10, the concentration ratio of IAA to CTAB is 1:(0.055-1.4).

Preferably, in step S10, the concentration ratio of PFCs to IAA is 1:(40-42).

Preferably, the process of step S10 comprises: mixing CTAB, IAA and PFCs at a concentration ratio of 1.4:1:0.024 and stirring for 5-15 min at the speed of 400-600 rmp to obtain a solution of ternary mixed self-assembled micelle.

Preferably, the solution of ternary mixed self-assembled micelle obtained in step S10 is charged into a photoreactor, the pH of the solution is adjusted to 5-7, and then a high-voltage mercury lamp is turned on to illuminate the solution of ternary mixed self-assembled micelle to implement photoreaction to degrade PFCs.

Preferably, the high-voltage mercury lamp is a mercury lamp with a power of 500 W.

Preferably, the photoreaction is performed at 20-30° C. for 2-3 h.

3. Beneficial Effects

Compared with the prior art, the present invention has the following beneficial effects:

(1) A method for degrading PFCs according to the present invention uses a positively charged CTAB solution as a bridge to form compact mixed self-assembled micelles of IAA and PFOA/PFOS, which are originally mutually exclusive, through electrostatic action. Surprisingly, it is found that the mixed self-assembled micelles closely combine PFOA/PFOS and IAA, greatly improving the utilization rate and reaction rate of hydrated electrons generated under the ultraviolet radiation to IAA in the photoreaction process, promoting the degradation of PFOA, and further improving the degradation efficiency.

(2) According to the method for degrading PFCs of the present invention, the hydrated electrons generated in the micelles are well protected due to they are wrapped in colloid, thus slowing down the quenching of the hydrated electrons by oxygen and protons, effectively inhibiting the influence of oxygen and protonspresent in the environment on the reduction and degradation of PFOA/PFOS, thus enabling the degradation reaction to occur under aerobic and acidic conditions and improving the adaptability to the environment.

(3) According to the method for degrading PFCs of the present invention, when performing photoreaction under ultraviolet irradiation, the mixed self-assembled micelles can polymerize quickly, and almost all of the organic substances in the system settle after the reaction. Therefore, the introduced CTAB and IAA do not cause secondary pollution to the environment, thus realizing the green and environment-friendly technology for degrading PFCs.

BRIEF DESCRIPTION OF THE DRAWINGS

FIG. 3 shows cryoelectron microscopy images of the binary system only with IAA and PFOA (a) and the ternary system with CTAB, IAA and PFOA (b) of the present invention;

FIG. 4 shows dynamic light scattering particle size diagram (a) and potential diagram (b) of the ternary system with 1 mM IAA, 0.024 mM PFOA and different concentrations of CTAB of the present invention;

FIG. 5 shows degradation diagram (a) and defluorination diagram (b) of PFOA by the mixed self-assembled micelle system of the present invention;

FIG. 9 shows particle size distribution diagram (a) and potential diagram (b) of the self-assembled system in the reaction process of the present invention;

FIG. 11 shows degradation diagram (a) and defluorination diagram (b) of PFOA by the mixed self-assembled system under different pH of the present invention; and FIG. 12 shows degradation diagram (a) and defluorination diagram (b) of PFOS by the mixed self-assembled system of the present invention.

DETAILED DESCRIPTION

The present invention is further described below with reference to specific embodiments.

The following is the detailed description of exemplary embodiments of the present invention with reference to the accompanying drawings. Although these exemplary embodiments are described in sufficient detail to enable those skilled in the art to implement the present invention, it should be understood that other embodiments may be implemented and various changes may be made to the present invention without departing from the spirit and scope of the present invention. The following more detailed description of the embodiments of the present invention is not intended to limit the claimed scope of the present invention, but is merely for illustration and does not limit the description of the characteristics and features of the present invention to suggest the best mode of implementing the present invention and is sufficient to enable those skilled in the art to implement the present invention. Therefore, the scope of the present invention is limited only by the appended claims.

A method for degrading PFCs according to the present invention comprises the following steps:

S10: respectively preparing 300 mL of 2 mM IAA solution, 100 mL of 5.6 mM CTAB solution and 10 mL of 1 g $L^{-1}$ (i.e. 2.4 mM) PFOA solution; taking 15 mL of 2 mM IAA solution, 0.29-7.5 mL of 5.6 mM CTAB solution and 0.3 mL of 2.4 mM PFOA solution and mixing, and then adding water to the volume of 30 mL; wherein the concentration ratio of IAA to CTAB is 1:(0.055-1.4) and the concentration ratio of PFCs to IAA is 1:(40-42); followed by stirring for 5-15 min at the speed of 400-600 rmp, and obtaining a solution of ternary mixed self-assembled micelle after uniform mixing;

S20: charging the solution of ternary mixed self-assembled micelle obtained in step S10 into cylindrical quartz photoreaction tubes (d=1 cm, h=15 cm), and adjusting the pH of the solution to 5-7, preferably 6; then, using a 500 W high-voltage mercury lamp as a light source to perform photoreaction on the solution of ternary mixed self-assembled micelle to degrade PFCs, and controlling the reaction to be performed at 20-30° C. for 2-3 h.

PFCs are degraded by the method of the present invention, so that the PFOA concentration can be reduced from 10 mg $L^{-1}$ to about 60 ng $L^{-1}$, and the degradation rate is close to 100%.

Figure 1:
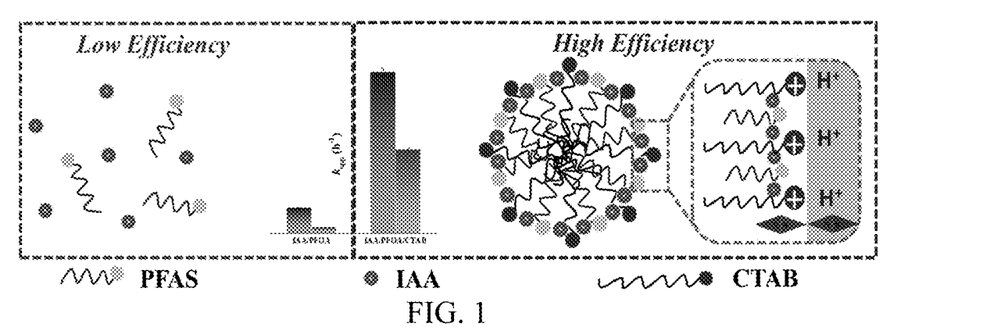
FIG. 1 is a schematic diagram showing the degradation of PFCs in the mixed self-assembled micelles of the present invention.

It should be noted that, as shown in FIG. 1, a certain amount of positively charged cationic surfactant CTAB is added into the mixed solution of IAA and PFCs which are both negatively charged, and the positively charged CTAB combines IAA and PFCs which are originally mutually exclusive to form compact self-assembled micelles through electrostatic action, and PFCs are rapidly degraded in the micelles under ultraviolet irradiation. On the one hand, the CTAB-induced mixed self-assembled micelles make IAA and PFCs more closely combined, which greatly improves the reaction rate of hydrated electrons generated by PFCs and IAA under illumination. On the other hand, the hydrated electrons generated in the micelles are well protected due to they are wrapped in colloid, thus slowing down the quenching of hydrated electrons by oxygen and protons; and which also improves the utilization efficiency of hydrated electrons and realizes the rapid degradation and defluorination of PFCs under aerobic and acidic conditions.

In addition, when ultraviolet irradiation is performed for photoreaction, the mixed self-assembled micelles can polymerize quickly; after the photoreaction is completed, the self-assembled micelles settle quickly, and almost all of the organic substances remaining in a system settle, so the introduced CTAB and IAA do not cause secondary pollution to the environment, thereby implementing the green and environment-friendly technology for degrading PFCs.

Example 1

In this example, the surface energies of IAA/PFOA/CTAB mixed micelle systems formed by adding different concentrations of CTAB were measured, with the steps as follows:

(1) the mixed systems containing 1 mM IAA, 10 mg $L^{-1}$ (0.024 mM) PFOA and CTAB with different concentrations (0-1.4 mM) were stirred at 500 rmp for 10 min to obtain mixed self-assembled micelle solutions; the concentrations of CTAB were 0, 0.027, 0.055, 0.082, 0.11, 0.14, 0.17, 0.22, 0.27, 0.41, 0.55, 0.82, 1.1, 1.4 mM respectively, and control solutions had only different concentrations of CTAB.

Figure 2:
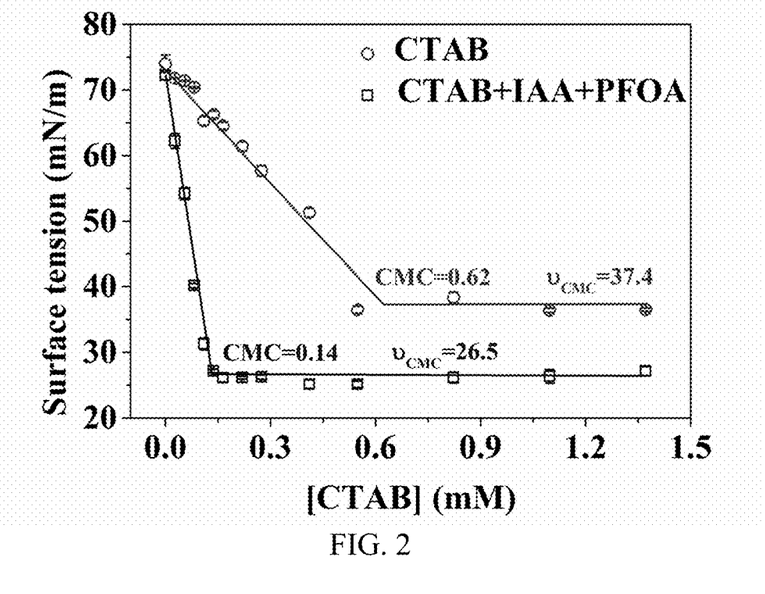
FIG. 2 is a surface tension diagram of alone CTAB solutions with different concentrations and the CTAB solution containing 1 mM IAA and 0.024 mM PFOA of the present invention.

(2) the pH of the mixed self-assembled micelle solutions and the control solutions obtained in Step (1) were adjusted to 6, and the surface energies were measured by using a surface tension meter, as shown in FIG. 2.

It can be concluded that the CMC value and the equilibrium surface tension value of the IAA/PFOA/CTAB mixed systems are significantly lower than those of the alone CTAB systems.

Example 2

In this example, the mixed self-assembled micelles induced by CTAB were shot by cryoelectron microscope, with the steps as follows:

(1) 15 mL of prepared 2 mM IAA solution, 0.75 mL of prepared 5.6 mM CTAB solution and 0.3 mL of prepared 1 g $L^{-1}$ PFOA solution were mixed and then water was added to the volume of 30 mL, and then stirred at 500 rmp for 10 min to obtain the mixed self-assembled micelle solution; meanwhile, 15 mL of 2 mM IAA solution and 0.3 mL of 1 g $L^{-1}$ PFOA solution were mixed and water was added to the volume of 30 mL as control solution.

Figure 3A:
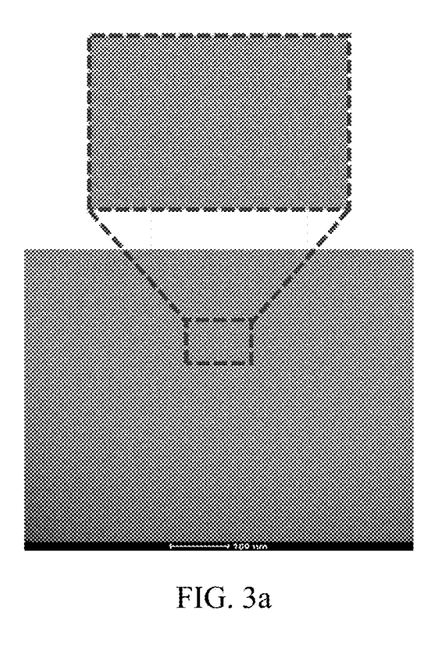

(2) the pH of the mixed self-assembled micelle solution and the control solution obtained in Step (1) were adjusted to 6, then 10 μL of the foregoing solutions were taken respectively and added to two different lace carbon films. The lace carbon films were quickly inserted into liquid nitrogen cooled ethane liquid for cooling, and the cooled sample films were put into the cryoelectron microscope for shooting, specifically as shown in FIGS. 3a-b.

Figure 3B:
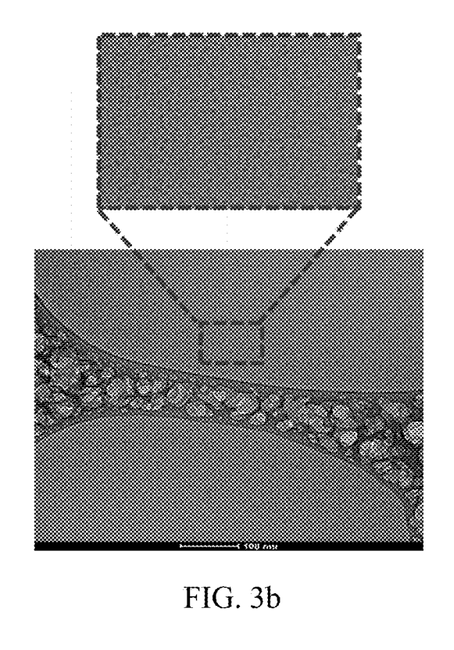

It can be concluded that self-assembled micelles are not formed in the mixed solution of IAA and PFOA without CTAB (FIG. 3a), and mixed self-assembled micelles are formed in the mixed solution containing CTAB, IAA and PFOA (FIG. 3b).

Example 3

In this example, the particle size and potential of generated micelles were measured by dynamic light scattering, with the steps as follows:

(1) the mixed systems containing 1 mM IAA, 10 mg $L^{-1}$ PFOA and CTAB with different concentrations were stirred at 500 rmp for 10 min to obtain mixed self-assembled micelle solutions, wherein the concentrations of CTAB were 0, 0.055, 0.14, 0.27, 0.82 and 1.4 mM respectively, and the mixed system with the CTAB concentration of 0 mM was used as a control solution.

Figure 4A:
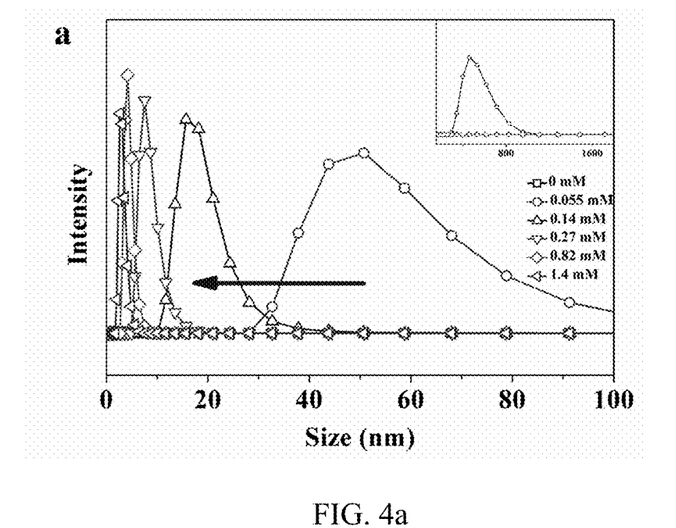
Figure 4B:
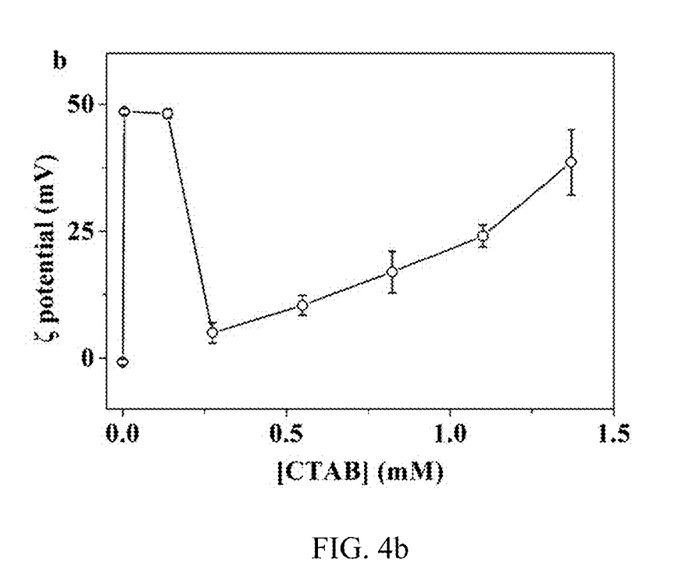

(2) the pH of the mixed self-assembled micelle solutions and the control solution obtained in Step (1) were adjusted to 6, and then 1 mL of the foregoing solutions were taken respectively to measure the particle sizes, specifically as shown in FIGS. 4a-b.

It can be concluded that the size of self-assembled micelles gradually decreases with the increase of concentration of CTAB added (FIG. 4a), while with the increase of the CTAB concentration, the potential of the systems are different (FIG. 4b), which may be caused by the difference of charge density on the micelle surface.

Example 4

In this example, the impact of mixed self-assembled micelles on PFOA degradation was investigated, with the steps as follows:

(1) mixed systems containing 1 mM IAA, 10 mg $L^{-1}$ PFOA and CTAB with different concentrations were stirred at 500 rmp for 10 min to obtain mixed self-assembled micelle solutions, wherein the concentrations of CTAB were 0.055, 0.14, 0.27, 0.82 and 1.4 mM respectively, and the solution only with IAA and PFOA and without CTAB was taken as a control solution.

Figure 5A:
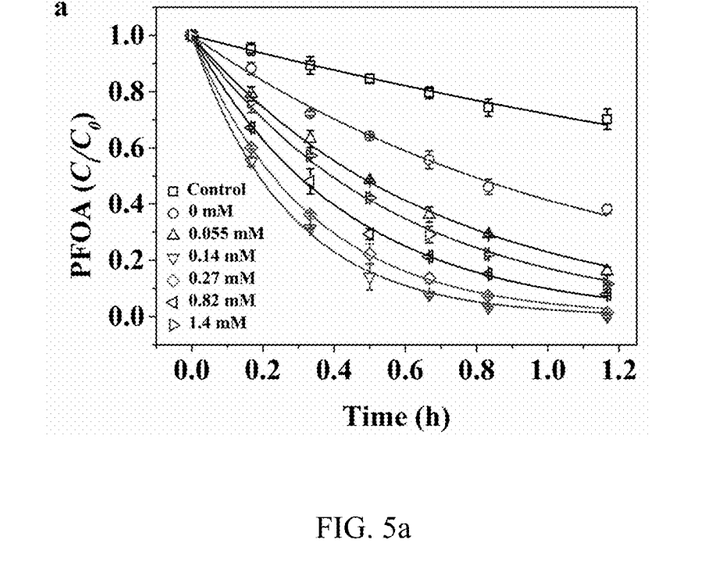
Figure 5B:
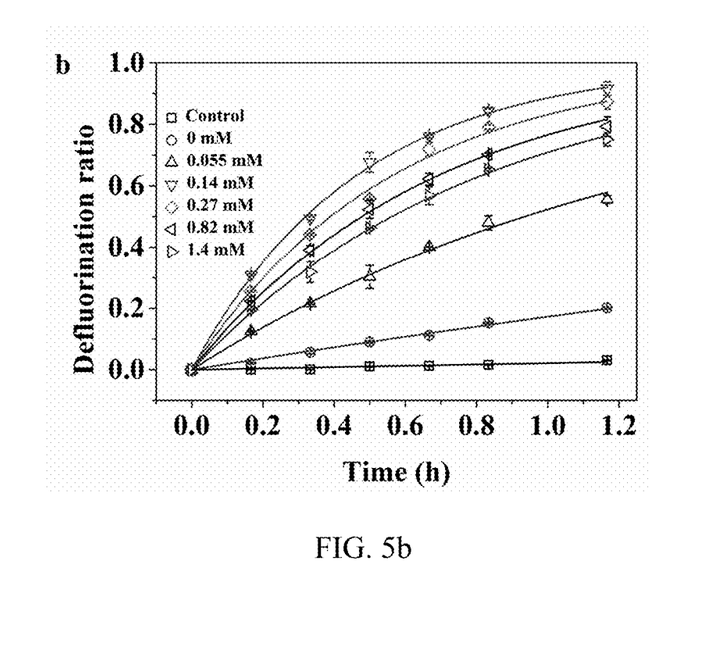

(2) the mixed self-assembled micelle solutions and the control solution in Step (1) were charged into cylindrical quartz photoreaction tubes (d=1 cm, h=15 cm), the pH values were adjusted to 6, and put in a photoreaction meter with a 500 W mercury lamp as a light source; the reaction was controlled to be performed at 25±2° C. for 2.5 h; the sampling times were set to 0 h, 0.33 h, 0.67 h, 1 h, 1.3 h, 1.7 h, 2 h and 2.5 h respectively; the sample was divided into two parts, one part was extracted with acetonitrile in the volume ratio of 1:2 and the content of remaining PFOA was measured by LC-MS/MS; the other part was filtered and the content of generated $F^-$ was measured by ion chromatography (IC) to calculate the degradation rate and defluorination rate of PFOA, the specific degradation and defluorination curves were shown in FIGS. 5a-b.

It can be concluded that the mixed self-assembled micelles significantly promote the light degradation and defluorination of PFOA, and the degradation and defluorination rate of PFOA is the fastest when 0.14 mM CTAB is added.

Example 5

In this example, the impact of mixed self-assembled micelles on the amount of hydrated electrons generated was investigated, with the steps as follows:

(1) mixed systems containing 1 mM IAA, 10 mg $L^{-1}$ PFOA and CTAB with different concentrations were stirred at 500 rmp for 10 min to obtain mixed self-assembled micelle solutions, and the solutions were aerated nitrogen to remove oxygen for half an hour, wherein the concentrations of CTAB were 0, 0.055, 0.14, 0.27, 0.82 and 1.4 mM respectively.

Figure 6:
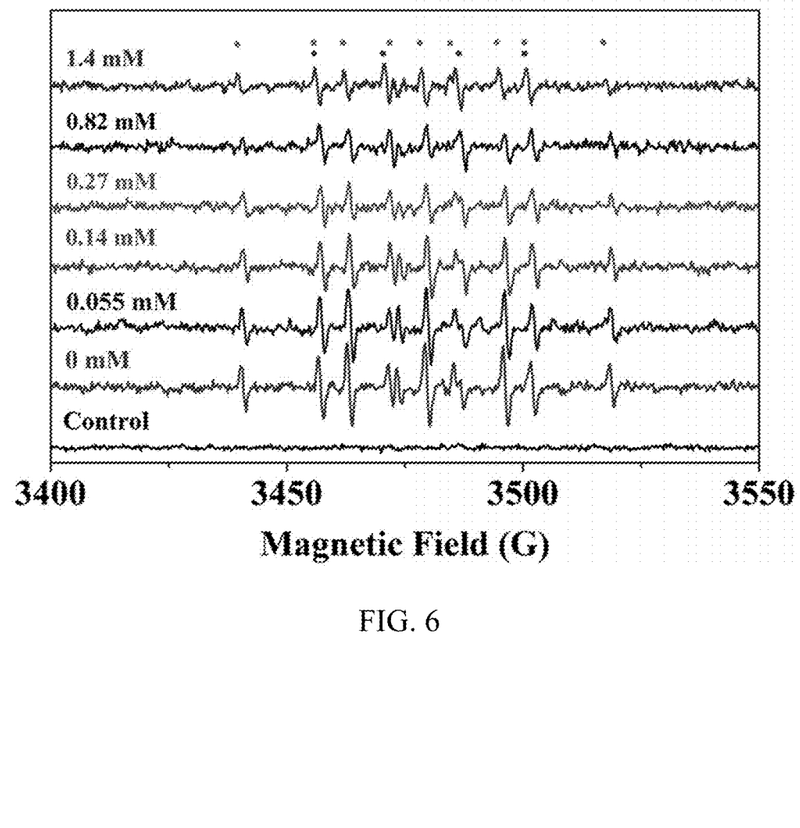
FIG. 6 is an electron paramagnetic resonance spectrogram of the present invention.
Figure 7A:
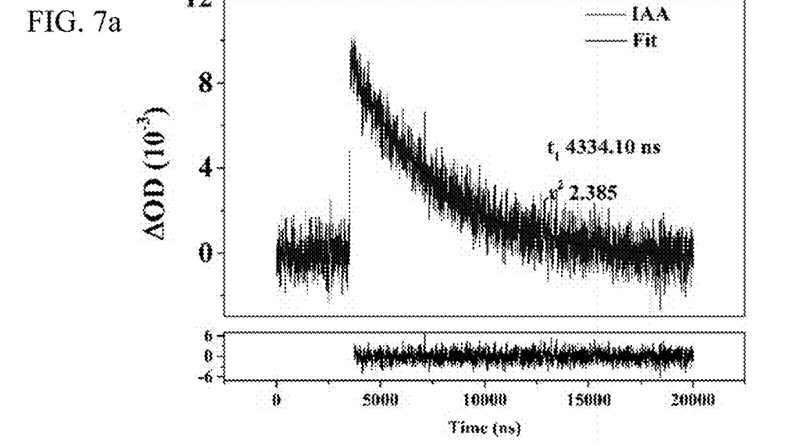
FIGS. 7a-f are laser flash photolysis diagram of the present invention.
Figure 7B:
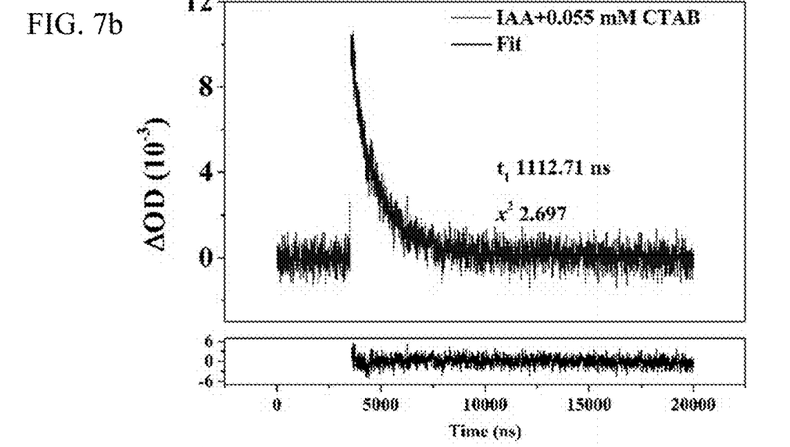
Figure 7C:
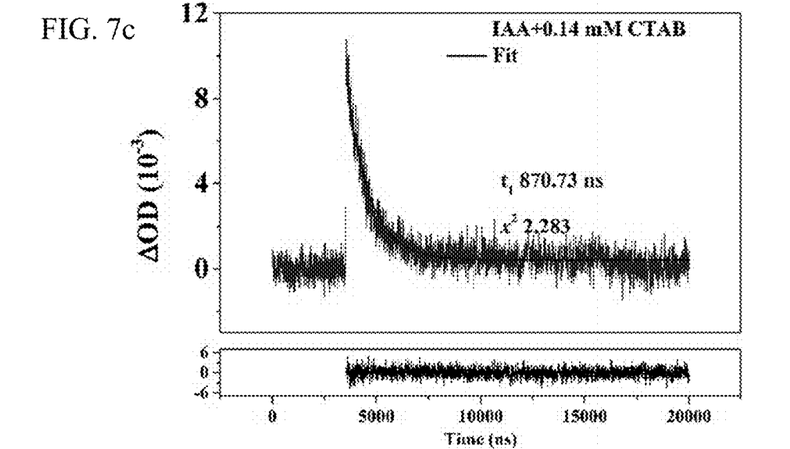
Figure 7D:
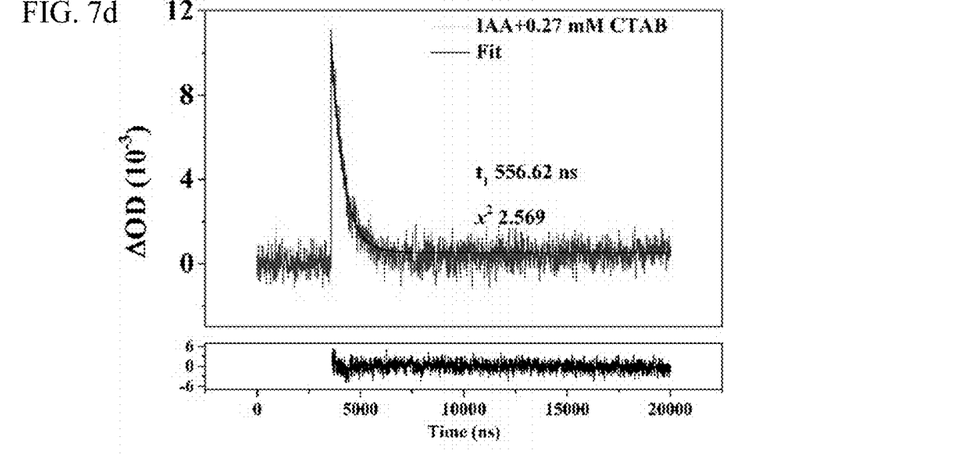
Figure 7E:
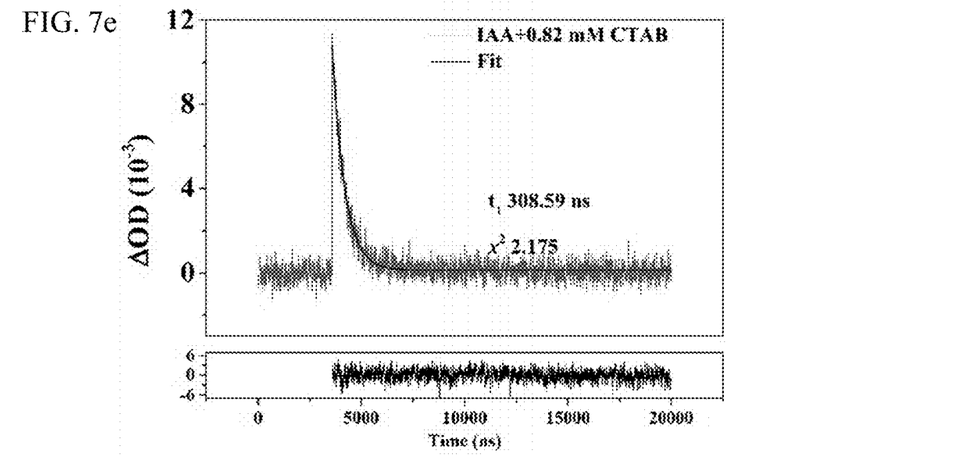
Figure 7F:
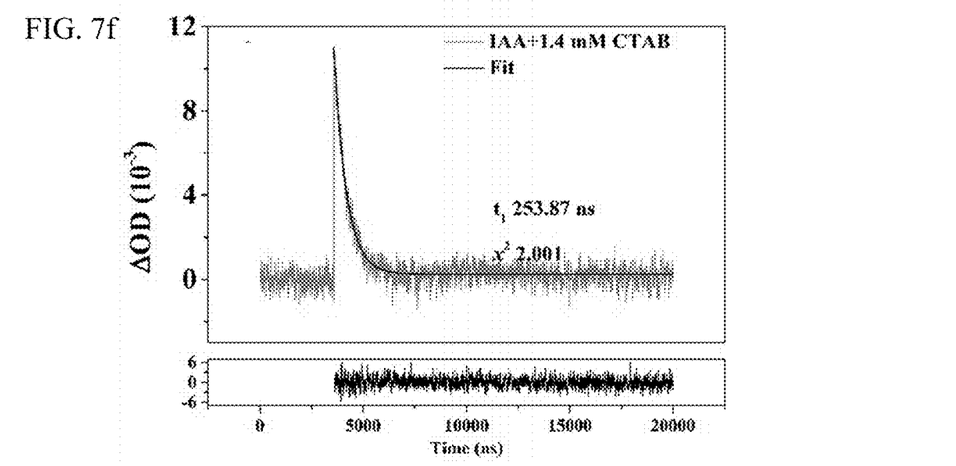

(2) the mixed self-assembled micelle solutions and the control IAA solution were transferred to two 20 mL glass tubes respectively, the pH of the solutions were adjusted to 6 with 0.1 mM NaOH, and hydrated electron trapping agent 5,5-dimethyl-1-pyrroline-N-oxide (DMPO) was added, wherein the DMPO concentration was 20 mM; after irradiation with a 180 W mercury lamp for 3.5 min, 20 μL of samples were taken and put into an electron paramagnetic resonance (EPR) spectrometer to detect free radical signals, specifically as shown in FIG. 6.

It can be concluded that mixed self-assembled micelles inhibit the generation of hydrated electrons.

Example 6

In this example, the decay rate of hydrated electrons in mixed self-assembled micelles was investigated, with the steps as follows:

(1) mixed systems containing 1 mM IAA, 10 mg $L^{-1}$ PFOA and CTAB with different concentrations were stirred at 500 rmp for 10 min to obtain mixed self-assembled micelle solutions, and the solutions were aerated nitrogen to remove oxygen for half an hour, wherein the concentrations of CTAB were 0, 0.055, 0.14, 0.27, 0.82 and 1.4 mM respectively.

(2) 3 mL of mixed self-assembled micelle solutions obtained in Step (1) were taken respectively and charged into 1 cm*1 cm*4 cm quartz cuvette; the solutions were aerated nitrogen for 30 min, and then the service lives of generated hydrated electrons after excitation with 266 nm exciting light were measured, specifically as shown in FIGS. 7a-f.

It can be concluded that the service lives of hydrated electrons in mixed self-assembled micelles are greatly shortened, which is caused by the rapid binding reaction between hydrated electrons and CTAB. The results also demonstrate that the ESR signal intensity of the hydrated electrons decreases after CTAB is added.

Example 7

In this example, changes of mixed self-assembled micelles in the reaction process were investigated, with the steps as follows:

(1) 15 mL of prepared 2 mM IAA solution, 0.75 mL of prepared 5.6 mM CTAB solution and 0.3 mL of prepared 1 g $L^{-1}$ PFOA solution were mixed and water was added to the volume of 30 mL, and then stirred at 500 rmp for 10 min to obtain a mixed self-assembled micelle solution.

Figure 8:
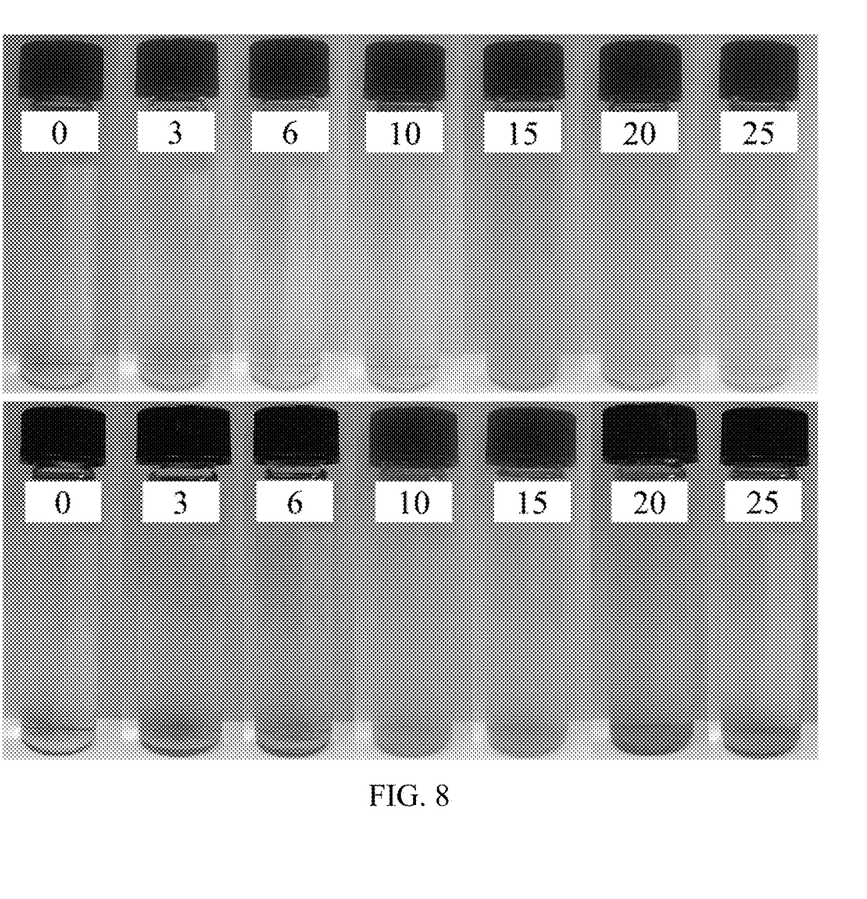
FIG. 8 shows photographs of the self-assembled system after the reaction and after settling for 30 min.

(2) the mixed self-assembled micelle solution obtained in Step (1) was charged into cylindrical quartz light reaction tube (d=1 cm, h=15 cm), the pH was adjusted to 6, and put in a photoreaction meter with a 500 W mercury lamp as a light source; the reaction was controlled to be performed at 25±2° C. for 25 min; the sampling times were set to 0 min, 3 min, 6 min, 10 min, 15 min, 20 min and 25 min respectively; and then the photos were taken (in FIG. 8, the upper shows the photograph of the solution after reaction, and the lower shows the photograph of the solution after settling for 30 min upon the completion of the reaction).

It can be concluded that the mixed self-assembled micelles undergo phase change after ultraviolet irradiation and eventually form precipitates.

Example 8

In this example, changes of the particle size and potential of mixed self-assembled micelles in the reaction process were investigated, with the steps as follows:

(1) 15 mL of prepared 2 mM IAA solution, 0.75 mL of prepared 5.6 mM CTAB solution and 0.3 mL of prepared 1 g $L^{-1}$ PFOA solution were mixed and water was added to the volume of 30 mL, and then stirred at 500 rmp for 10 min to obtain a mixed self-assembled micelle solution.

Figure 9A:
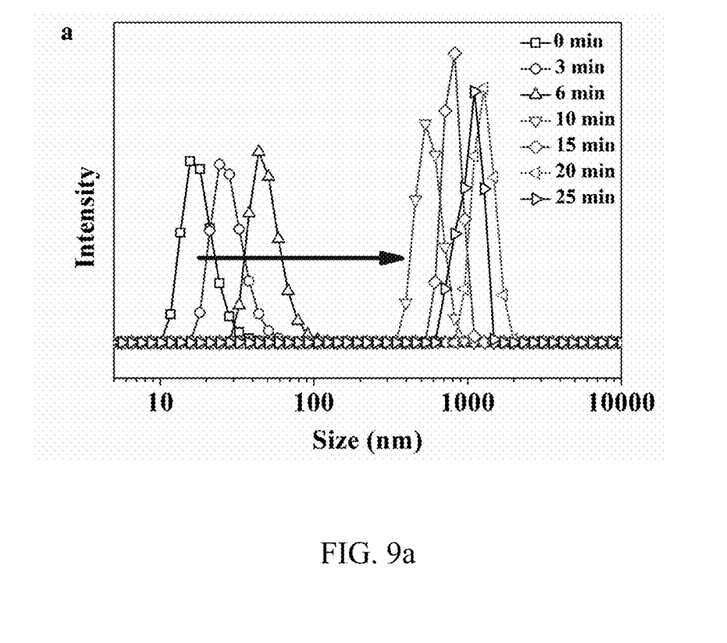
Figure 9B:
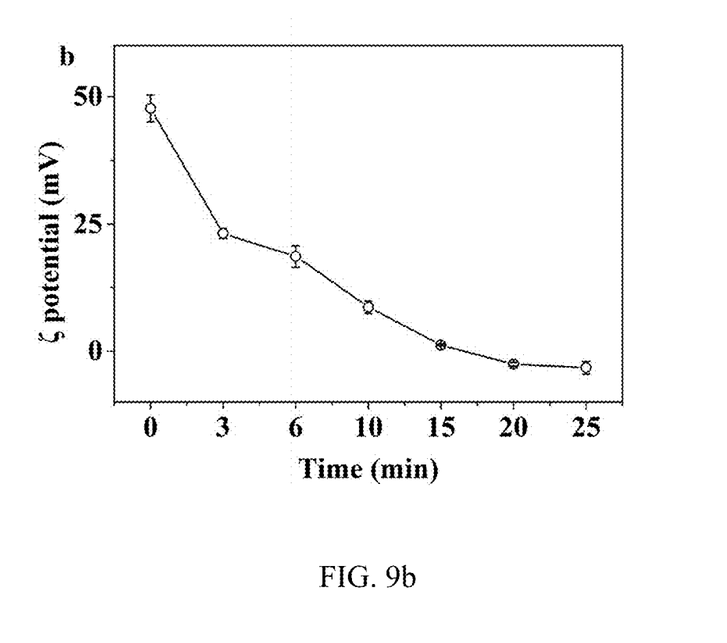

(2) the mixed self-assembled micelle solution obtained in Step (1) was charged into cylindrical quartz photoreaction tube (d=1 cm, h=15 cm), the pH was adjusted to 6, and put in a photoreaction meter with a 500 W mercury lamp as a light source; the reaction was controlled to be performed at 25±2° C. for 25 min; the sampling times were set to 0 min, 3 min, 6 min, 10 min, 15 min, 20 min and 25 min respectively; and then the changes of particle size in a system were monitored, specifically as shown in FIGS. 9a-b.

It can be concluded that the particle size of mixed self-assembled micelles increases obviously and potential decreases continuously after ultraviolet irradiation, which indicates that the final precipitate is mainly formed by aggregation of micelles.

Example 9

In this example, changes of DOC of a mixed self-assembled micelle system in the reaction process were investigated, with the steps as follows:

(1) 15 mL of prepared 2 mM IAA solution, 0.75 mL of prepared 5.6 mM CTAB solution and 0.3 mL of prepared 1 g L$^{-1}$ PFOA solution were mixed and water was added to the volume of 30 mL, and then stirred at 500 rmp for 10 min to obtain a mixed self-assembled micelle solution.

Figure 10:
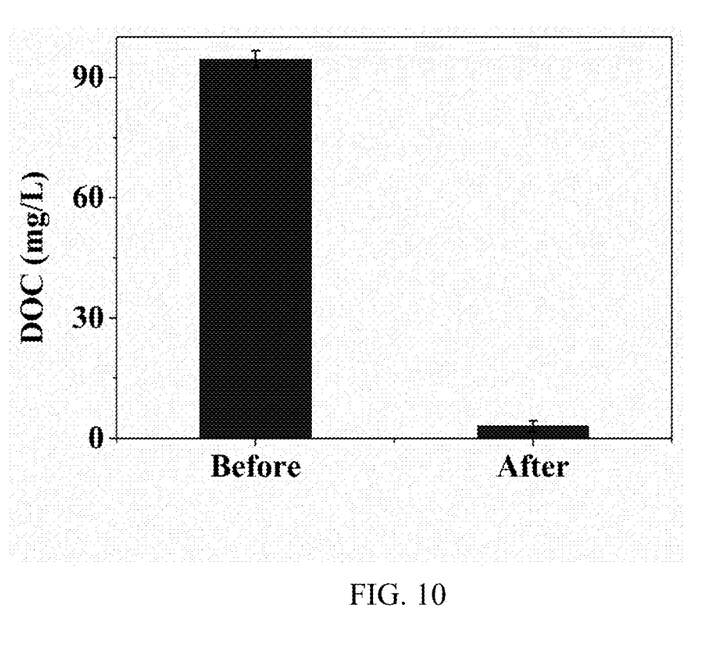
FIG. 10 is a diagram showing the variation of dissolved organic carbon (DOC) of the self-assembled system in the reaction process system of the present invention.

(2) the mixed self-assembled micelle solution obtained in Step (1) was charged into cylindrical quartz photoreaction tube (d=1 cm, h=15 cm), the pH was adjusted to 6, and put in a photoreaction meter with a 500 W mercury lamp as a light source; the reaction was controlled to be performed at 25±2° C. for 2.5 h; the sampling times were respectively set to be 0 h and 2.5 h; 9 mL of the solution was taken into a 10 mL glass bottle at each time point, standing for 30 min and then the supernatant was removed to measure DOC, specifically as shown in FIG. 10.

It can be concluded that the DOC value of the system decreased from about 94 mg L$^{-1}$ to about 3 mg L$^{-1}$ after the reaction, demonstrating that the longer the reaction time observed by the above scanning electron microscope, the more the retentate.

Example 10

In this example, the impact of pH on the mixed self-assembled micelle system was investigated, with the steps as follows.

(1) 15 mL of prepared 2 mM IAA solution, 0.75 mL of prepared 5.6 mM CTAB solution and 0.3 mL of prepared 1 g L$^{-1}$ PFOA solution were mixed and water was added to the volume of 30 mL, and then stirred at 500 rmp for 10 min to obtain a mixed self-assembled micelle solution.

Figure 11A:
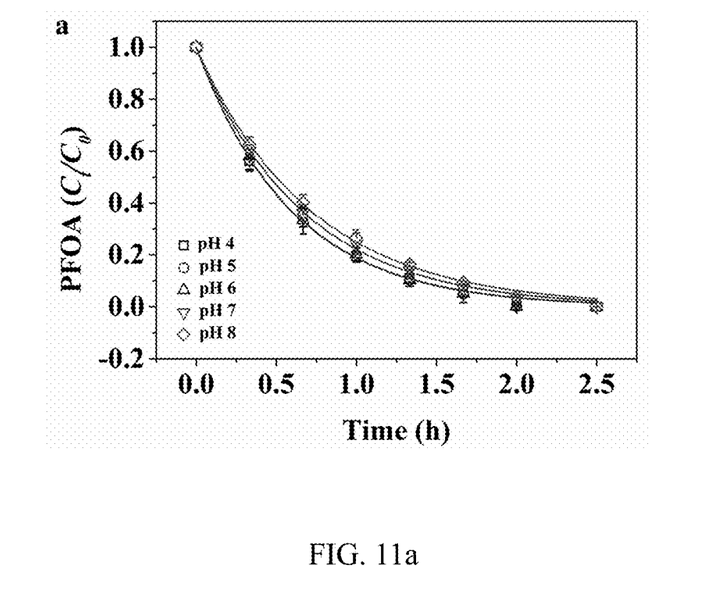
Figure 11B:
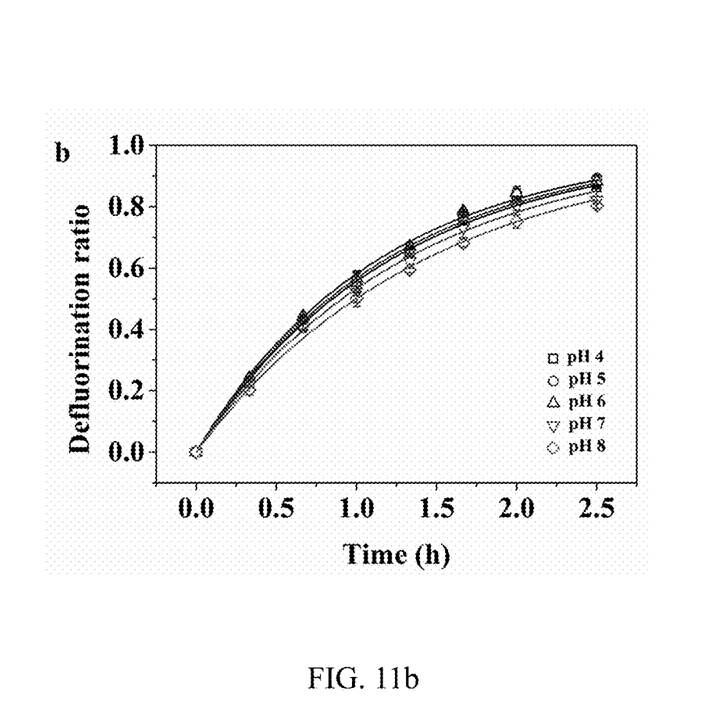

(2) the mixed self-assembled micelle solution obtained in Step (1) was charged into cylindrical quartz photoreaction tubes (d=1 cm, h=15 cm), the initial pH values were adjusted to 4, 5, 6, 7 and 8 respectively, and put in a photoreaction meter with a 500 W mercury lamp as a light source; the reaction was controlled to be performed at 25±2° C. for 2.5 h; the sampling times were set to 0 h, 0.33 h, 0.67 h, 1 h, 1.3 h, 1.7 h, 2.0 h and 2.5 h respectively; the sample was divided into two parts, one part was extracted with acetonitrile at the volume ratio of 1:2 and then the content of remaining PFOA was measured by high performance liquid chromatography (HPLC); the other part was filtered and then the content of generated F$^-$ was measured by IC to calculate the degradation rate and defluorination rate of PFOA, the specific degradation and defluorination curves were shown in FIGS. 11*a-b*.

It can be concluded that pH has little impact on the system, which is mainly due to the repulsion of the positive electricity on the micelle surface to protons in the solution, thus protecting the reactions inside the micelles.

Example 11

In this example, the impact of mixed self-assembled micelles on PFOS degradation was mainly investigated, with the steps as follows:

(1) 15 mL of prepared 2 mM IAA solution, 0.75 mL of prepared 5.6 mM CTAB solution and 0.3 mL of prepared 1 g L$^{-1}$ PFOA solution were mixed and water was added to the volume of 30 mL, and then stirred at 500 rmp for 10 min to obtain a mixed self-assembled micelle solution, meanwhile, the control solution is 30 mL of 10 mg L$^{-1}$ PFOS solution.

Figure 12A:
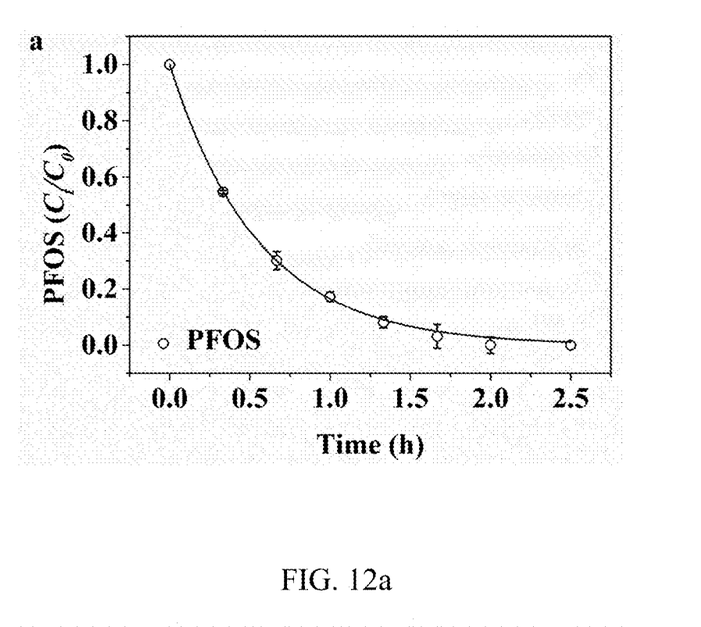
Figure 12B:
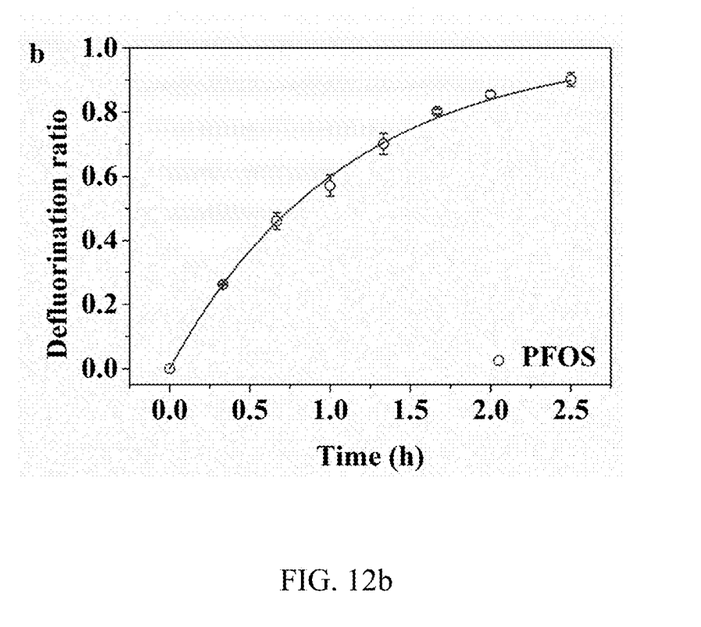

(2) the mixed self-assembled micelle solution and the control solution in Step (1) were charged into cylindrical quartz photoreaction tubes (d=1 cm, h=15 cm), the pH values were adjusted to 6, and put in a photoreaction meter with a 500 W mercury lamp as a light source; the reaction was controlled to be performed at 25±2° C. for 2.5 h; the sampling times were set to 0 h, 0.33 h, 0.67 h, 1 h, 1.3 h, 1.7 h, 2 h and 2.5 h respectively; the sample was divided into two parts, one part was extracted with acetonitrile at the volume ratio of 1:2, and then the content of remaining PFOS was measured by LC-MS/MS; the other part was filtered and then the content of generated F$^-$ was measured by IC to calculate the degradation rate and defluorination rate of PFOS, the specific degradation and defluorination curves were shown in FIGS. 12*a-b*.

It can be concluded that the mixed self-assembled micelles are not only effective for the degradation of PFOA, but also effective for the light degradation and defluorination of PFOS.

In summary, the method for degrading PFCs according to the present invention adopts a novel self-assembled micelle system, so that PFCs are rapidly degraded and defluorinated in the micelles, thereby improving the degradation efficiency of PFCs. And the method is a green and environment-friendly PFC degradation method, which is suitable for wide application.

The invention claimed is:

1. A method for degrading perfluorinated compounds (PFCs), comprising the following steps:
   S10: uniformly mixing cetyltrimethylammonium bromide (CTAB), indoleacetic acid (IAA) and PFCs to obtain ternary mixed self-assembled micelles; and
   S20: illuminating the ternary mixed self-assembled micelles obtained in step S10 by a high-voltage mercury lamp to implement photoreaction to degrade PFCs.

2. The method for degrading PFCs according to claim 1, wherein in step S10, the concentration ratio of IAA to CTAB is 1:(0.055-1.4).

3. The method for degrading PFCs according to claim 1, wherein in step S10, the concentration ratio of PFCs to IAA is 1:(40-42).

4. The method for degrading PFCs according to claim 1, wherein the process of step S10 comprises: mixing CTAB, IAA and PFCs at a concentration ratio of 1.4:1:0.024 and stirring for 5-15 min at the speed of 400-600 rmp to obtain a solution of ternary mixed self-assembled micelle.

5. The method for degrading PFCs according to claim 1, wherein the process of step S20 comprises: charging the solution of ternary mixed self-assembled micelle obtained in step S10 into a photoreactor, adjusting the pH of the solution to 5-7, and then turning on a high-voltage mercury lamp to illuminate the solution of ternary mixed self-assembled micelle to implement photoreaction to degrade PFCs.

6. The method for degrading PFCs according to claim 5, wherein the high-voltage mercury lamp is a mercury lamp with a power of 500 W.

7. The method for degrading PFCs according to claim 5, wherein the photoreaction is performed at 20-30° C. for 2-3 h.

* * * * *